(12) United States Patent
Haven et al.

(10) Patent No.: US 6,462,813 B1
(45) Date of Patent: *Oct. 8, 2002

(54) SURFACE DEFECT INSPECTION SYSTEM AND METHOD

(75) Inventors: G. Neil Haven, Stockbridge; Myron Czubko, Ann Arbor, both of MI (US)

(73) Assignee: Perceptron, Inc., Plymouth, MI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/833,926

(22) Filed: Apr. 10, 1997

Related U.S. Application Data

(63) Continuation-in-part of application No. 08/673,926, filed on Jul. 1, 1996, now abandoned.
(60) Provisional application No. 60/015,406, filed on Apr. 12, 1996.

(51) Int. Cl.$^7$ .............................................. G01N 21/00
(52) U.S. Cl. .................... 356/237.2; 356/371; 356/446; 348/128; 250/559.48
(58) Field of Search ................................ 356/237, 394, 356/371, 445, 446, 429–431, 237.1, 237.2; 250/559.47, 559.01, 559.05, 559.06, 559.48; 348/125, 126, 128

(56) References Cited

U.S. PATENT DOCUMENTS

| | | | |
|---|---|---|---|
| 4,376,583 A | * 3/1983 | Alford et al. | 356/431 |
| 4,507,564 A | * 3/1985 | Shimada | 356/431 |
| 4,918,321 A | 4/1990 | Klenk et al. | 250/571 |
| 4,966,455 A | * 10/1990 | Avni et al. | 356/446 |
| 5,237,404 A | 8/1993 | Tanaka et al. | 358/106 |
| 5,726,705 A | 3/1998 | Imanishi et al. | |
| 5,734,742 A | 3/1998 | Asaeda et al. | |

* cited by examiner

*Primary Examiner*—Hoa Q. Pham
(74) *Attorney, Agent, or Firm*—Harness, Dickey & Pierce, P.L.C.

(57) ABSTRACT

A system and method for detecting defects on a painted workpiece surface. The system includes an elongated line of light having a pair of sharp transition zones. The line of light falls onto a moving substrate containing a plurality of workpieces to be inspected. An area detector receives light scattered by the workpiece surface. A first image is captured proximate one edge of the line of light and a second image is captured proximate the other. A defect on the workpiece produces characteristic shadow or backscatter patterns which vary between the first and second images. The shadow and backscatter patterns cause variations in the amplitude of light detected by the detector. The image data is then digitized and electronically processed by software which recognizes each defect, and characterizes the defect by type and/or size.

15 Claims, 10 Drawing Sheets

SURFACE DEFECT INSPECTION SYSTEM AND METHOD

CROSS REFERENCE TO RELATED APPLICATIONS

This application is a continuation-in-part of U.S. Ser. No. 08/673,926, filed Jul. 1, 1996, now abandoned which, in turn, is based on provisional application Ser. No. 60/015,406, filed on Apr. 12, 1996, the disclosure of which is hereby incorporated by reference.

FIELD OF THE INVENTION

This invention concerns the field of automated inspection systems, and, particularly, a system and method useful for scanning a painted surface and detecting defects thereon.

DESCRIPTION OF THE RELEVANT PRIOR ART

Quality control is an important component of automated production processes. Like the products of the production processes which it scrutinizes, quality control has become increasingly automated over time. For example, automated visual inspection systems, rather than human inspectors, are increasingly being employed to perform repetitive visual scanning of workpieces in order to detect any flaws therein.

In particular, a number of prior art automated scanning systems have been developed which are specifically intended to inspect the surface of a workpiece to detect defects and blemishes in the painted surface thereof. For example, U.S. Pat. No. 5,367,378 to Harding et al. discloses an optical inspection system and method for evaluating the surfaces of large contoured panels. The method involves providing an illumination means for projecting a pattern of lines having a periodic configuration with features having a separation period. A camera records an image of the pattern of lines as reflected from the surface being inspected. The recorded image is evaluated and quantified by calculating a slope of a defect observed by the camera using a specified mathematical relationship. The distance between the illuminated pattern and the surface are used to calculate the defect slope, and a defect depth value is generated using a specific relationship dependent on the length of the defect area visually recognizable from the reflected image and the calculated defect slope.

U.S. Pat. No. 5,389,794 to Allen et al. discloses a surface pit and mound detection and discrimination system. The system scans a beam of radiation over the surface to be inspected, and includes a mechanism for separately sensing radiation scattered from the surface in the near and far specular regions in order to differentiate between pits and mounds and other types of defects. The system includes means for detecting a local slope on the surface from radiation scattered from the surface in the near specular region and for differentiating between whether said beam of radiation is scanning a pit or a mound.

U.S. Pat. No. 5,461,474 to Yoshii et al. discloses an inspection apparatus for detecting foreign matter on a surface having first and second spaced lines. The surface is scanned by a light beam in a direction orthogonal to the lines, and the size of the light beam is less than the interval between the two lines. The system includes detection means for detecting light reflected from the surface from the scanning and producing first and second signals corresponding to the scan of the first surface line and the second surface line, respectively. Signal processing means are provided for processing a correlation between the first and second signals and detecting whether foreign matter exists on the surface. This system is particularly useful for inspecting semiconductor devices having a circuit pattern formed thereon. The "first and second lines" on the surface to be inspected are, thus, part of the circuit pattern. The system has no particular utility for inspecting surfaces which do not include orthogonal patterns of lines and which contain defects which do not isotopically scatter impinging light. Such limitations render this system particularly unsuitable for inspecting irregular parts having large painted surfaces.

U.S. Pat. No. 4,918,321 to Klenk et al. discloses a method for the detection of blemishes on the surface of the object. The system uses a strip of light which is moved over the surface of the workpiece. Striplike sections of the surface being inspected are in each case recorded stepwise in the region of the strip of light, the step size of successive recordings being smaller than the width of the strip of light. The light reflected from the surface is directed onto an opto-electronic video camera by means of a movable reflecting means which controls the increment of movement between adjacent images. Since the Klenk system relies on a movable reflecting means, this creates the difficult problem of coordinating movement of the reflecting means over the surface of the workpiece if the surface is curved and complex.

U.S. Pat. No. 5,237,404 to Tanaka discloses a surface defect inspection system which interrogates the workpiece surface with radiating light having a predetermined change pattern. A camera is arranged for receiving an image of the irradiating, structured light which is reflected by the surface. The structured light contains gradations in intensity. The system looks for disruptions in the pattern of the structured light by taking partial derivatives of the wave form of the video signal.

Ideally, an automated system useful for inspecting workpieces having painted surfaces, such as vehicle body panels, should possess several important characteristics. First, the system should be able to isolate and detect individual flaws in the painted surface such as are caused by dirt or other foreign substances, pinholes or scratches in the paint finish, etc. Thus, it is important that the system be able to distinguish between defects which are raised or elevated above the paint surface (often caused by dirt or other foreign particles) and defects which are depressed below the nominal paint surface (such as caused by interruptions in the paint coat). Furthermore, it would be highly advantageous if such a system were able to characterize the defects by size so that only those body parts having defects larger than a certain reference size would need to be rejected.

Many painted workpieces such as vehicle body panels have certain structural features, such as, for example, cutouts for the door handle on a side body panel. Each such panel can be expected to have the same cutout in the same location. Thus, it would be highly desirable for an automated inspection system to be able to distinguish between these expected interruptions in the surface and true defects.

SUMMARY OF THE INVENTION

The present system and method have been designed to provide the desirable characteristics of an automated inspection system described above. Disclosed herein is a system and method for detecting defects on a surface, and particularly on a painted surface such as an automobile body panel. The system is capable of characterizing surface defects in a number of ways, including by size of the defect and by surface elevation of the defect (that is, whether it is a crater or a piece of foreign matter). The system is also capable of "learning" to recognize known features on the workpiece, such as, for example, a cutout for a door handle on a side auto body panel.

The system of the present invention comprises three main parts. The first part is the optical components, including a light source capable of projecting a line of light having leading and trailing edges or transitions from dark to bright. In one embodiment, the light source is a diffuse light source which radiates light through a slit to produce a line of light. The width of the slit is chosen with some care to meet the dual criteria of being wide enough that the surface roughness of the paint on the workpiece to be inspected (the "orange peel") does not throw a shadow, yet narrow enough that the more severely sloped dirt particles and craters do throw shadows. The system uses differences in the intensity of the light reflected back from the surface of the workpiece to detect dirt or other foreign particles in the paint. It would be undesirable for the system to mistake natural surface roughness of the paint for actual defects. In one embodiment, the system detects shadows cast by defects. In an alternate embodiment, the system detects light backscattered by dirt or other foreign particles in the paint. In yet another embodiment, the system detects both shadows cast by defects and the light backscattered by defects.

A moving substrate carries a succession of workpieces in a linear direction, the direction of travel of the substrate being perpendicular to the line of light projected from the light source. Thus, workpieces that are traveling on the substrate will sequentially pass through the line of light at right angles with respect thereto. Any given position on a workpiece will first pass through the trailing edge of the projected line of light and subsequently through the leading edge thereof.

A detector is provided which has a field of view that includes the area illuminated by the line of light. Since the workpieces travel in a direction perpendicular to the line of light, the detector will successively image all portions of each workpiece as the workpiece travels along with the substrate. The detector is further operative to produce signals which vary as the amplitude of the light scattered (either reflected and/or backscattered) by the surface onto the detector varies in amplitude. In a preferred embodiment, the detector is a charge coupled device detector including a linear array of charged coupled devices.

In the embodiment of the invention in which defects are detected by the shadows they throw, each location on the workpiece is imaged at least twice while traveling through the line of light. A first image is captured when the location is in the line of light and proximate the trailing edge thereof; a final image is captured when the location is proximate the leading edge of the line of light.

In the embodiment of the invention in which defects are detected by the light which they scatter back into the detector, each location on the workpiece is imaged at least twice while traveling outside the line of light.

The system of the present invention further includes means for adjusting the image processing to the rate of travel of the substrate. Depending on the production environment, the substrate may travel at varying rates of speed. The faster that the substrate (and workpieces carried thereon) travels, the further each location on a workpiece will travel during one captured image of the detector. In the embodiment of the invention in which defects are detected by shadows they throw, $\Delta_t$ (the time interval between scans) must be less than one-half the time it takes a location on the workpiece to travel from a position proximate the leading edge of the line of light to a position proximate the trailing edge thereof.

The second portion of the system is image processing equipment. First, the signal produced by the detector is digitized. The signals are converted from a two-dimensional data stream into a three-dimensional array by providing memory locations corresponding to each position on a three-dimension array in which the digital data is stored. If there is a defect at a location on the workpiece, the defect causes a variation in the amplitude of the light scattered from the workpiece surface onto the detector. This variation in amplitude is detected by the detector, digitized, and stored as described. Moreover, because the defect is imaged at least twice, each defect generates two separate sets of digital data, both of which are stored by the system. However, because the angle of light incident on the defect is different for each of the two images (since the defect is moving relative to the light source), the two sets of data representing shadows cast by the defect in one embodiment, or light backscattered by the defect in another embodiment, in the first and second images are slightly different.

The data is subjected to further digital processing in order to perform a correlation between the output signals from the detector gathered during the two captured images. In one embodiment of the system and method of the present invention, the two sets of image data are first passed through a finite impulse response filter (FIR) whose characteristic spatial frequency response is tuned to the rate of travel of the substrate. This serves to isolate and amplify the variation in amplitude caused by the defect. The filtered signals are then subjected to a subtraction (one set of data is subtracted from the other) to achieve a composite set of data. However, it is to be understood that these steps of filtering and subtracting may be performed in reverse order, in certain cases, so that the subtraction operation is performed first, and the composite signal is then passed through the FIR.

After the image has been processed, it is then subjected to the third element of the system, namely, post processing. Post processing is performed in a computer programmed with a software program capable of recognizing processed image data which represents defects, and classifying defects so identified by a particular characteristic, such as size, or surface elevation. For example, if the defect is a crater, then it will cast different and unique shadow patterns in each of the first and second images, resulting in a characteristic composite shadow pattern unique for craters. The characteristic patterns for craters are stored in the software. The program compares the processed image data with the stored data and determines whether the defect is a crater. The software can also store characteristic shadow patterns for other types of defects (such as bumps or pieces of foreign debris) so that the software can compare the processed image data and, again, determine whether the defect is an elevated defect.

The post processing software is also capable of being "taught" to recognize known surface variations in the workpieces. The system of the present invention can be used in a trial run with a plurality of workpieces (such as auto body side panels) which all have, for example, a door handle cut out in the same position. The post processing software can identify this particular characteristic on every workpiece and learn to expect it in a particular workpiece location. After the trial run, the system will subtract this known characteristic every time it processes the images for a new workpiece since the software has "learned" to expect this particular feature in this particular location. Since the system of the present invention is capable of learning to distinguish expected surface variations from unexpected ones, it can be used to inspect a wide variety of workpiece types, even those which are highly irregular. Thus, the system and method of the present invention display extreme versatility.

BRIEF DESCRIPTION OF THE DRAWINGS

The following detailed description is best understood with reference to the following drawings in which.

DETAILED DESCRIPTION OF THE PREFERRED EMBODIMENTS

Figure 1:
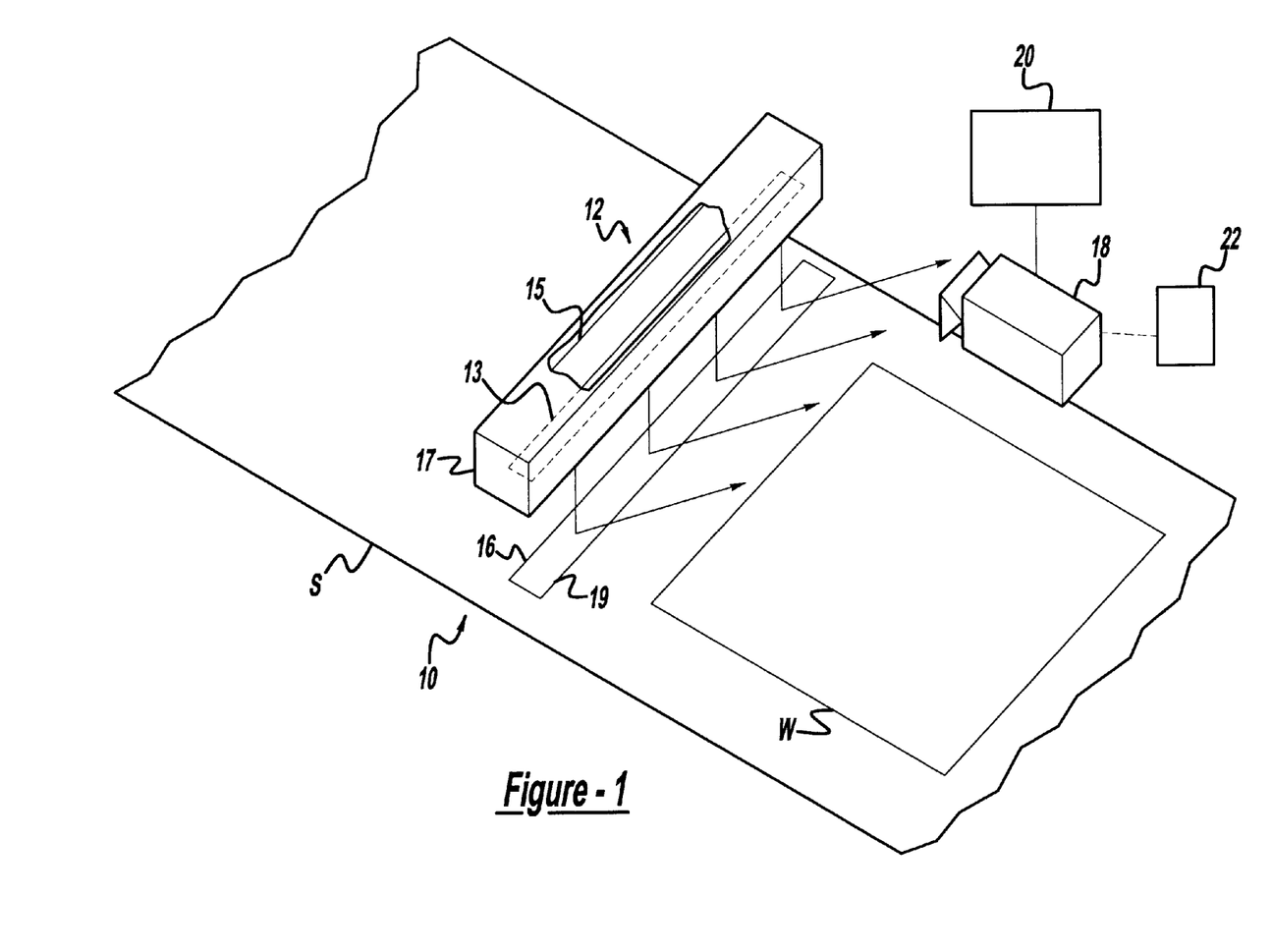
FIG. 1 is a perspective view of a surface inspection system according to the present invention.

Throughout the following detailed description, like numerals are used to reference the same elements of the present invention shown in multiple figures thereof. Referring now to the drawings, and in particular to FIG. 1, there is shown a perspective view of a surface inspection system 10 constructed according to the principles of the present invention. The inspection system 10 includes a light source 12 which emits an elongated line of diffuse light 14. Preferably, the source 12 includes a housing 13 containing a linear lamp 15. The housing 13 has an elongated slit 17 formed in the bottom thereof through which the line of light 14 is emitted. Preferably, the width of slit 17 is selected so that it is wide enough that the natural surface roughness or "orange peel" of a painted surface being inspected does not cast a shadow, yet narrow enough that dirt particles, other foreign matter, and breaks in the painted surface do cast shadows.

Preferably, the light source 12 comprises a fluorescent lamp 15 diffused through a thin (0.005 inches) sheet of diffusing film, such as that produced by the Plastic Films Company. The fluorescent lamp 15 is driven by a Mercron, Inc. lamp controller at a high frequency (20,000 Hz) so that several periods of light oscillation from the lamp occur during the integration time of the detector. The length of the slit 17 is chosen so that the length of the field of view of detector 18 (preferably, a CCD camera manufactured by Pulnix Corporation) is fully illuminated.

In an alternative embodiment, in which defects are detected by the light they scatter back to the detector 18 rather than the shadows they throw, slit 17 and the sheet of diffusing film may be omitted.

A moving substrate S supports a plurality of workpieces W. The direction of travel (indicated by the arrow) of the substrate S is perpendicular to the line of light 14, and the light source 12 is disposed such that line of light 14 falls onto moving substrate S. Typically, the substrate S will be a conveyor belt or the like which is used to convey a plurality of workpieces W through an automated production environment.

The line of light 14 has two "edges" or zones of sharp transition from light to darkness. These edges include leading edge 16 and trailing edge 19. A defect D in the painted surface of workpiece W will, as it is carried along in the direction of the arrow by substrate S, first pass through the trailing edge 19 of the line of light 14, and subsequently pass out of the line of light 14 through leading edge 16. For example, in FIG. 2A (which shows a detailed view of a portion of the substrate S with workpiece W thereon), defect D has just entered line of light 14 at time $T_0$ and lies proximate trailing edge 19. In contrast, as is shown in the similar view of FIG. 2B, a defect D at time $T_1$ is about to pass out of the line of light 14 and is now proximate leading edge 16. If the time interval between the positions of the defect shown in FIGS. 2A and 2B is $\Delta_T$, then $T_1=T_0+\Delta_T$.

The detector 18 is mounted above the moving substrate S and is positioned so that it views the reflection of the line of light 14 from the surface of the workpiece W being inspected. In an alternate configuration the detector 18 is mounted above the moving substrate S and is positioned so that it views the light backscattered from the surface of the workpiece being inspected by the line of light 14. The detector 18 is focused on the surface, and its integration time is set so short that the smallest defect to be detected travels no more than one pixel during the time of integration of the imaging array. FIGS. 2A and 2B illustrate the images seen by the camera at, respectively, times $T_0$ and $T_1$. The signal from the detector 18 is digitized in a computer provided with a combination digitizer/digital-signal-processor, such as is sold by Spectrum, Inc. In a manner well known in the prior art, the signal from the detector 18 is converted into a two-dimensional stream of digital data which is then converted into a three-dimensional array of pixels (arrayed in rows and columns) which are stored at memory locations in the computer 20.

The system also includes means 22 for adjusting the frequency of operation of the system. This is done by tuning the image processing algorithm to the rate of travel of the moving substrate, as measured for example by an encoder 22, S so that when the system captures a first image of a location on the workpiece containing a surface flaw (such as the image showing the defect D in FIG. 2A) at time $T_0$ it can predict the location of the surface flaw in a second image at time $T_1$ (when defect D is in the position of FIG. 2B). By adapting the image processing algorithm it is meant that the system measures the speed of the moving substrate and tunes the response of the FIR filter to match the spatial periodicity of a defect on the substrate moving at the measured speed and sampled at the image rate of the detector ($\Delta_t=T_0-T_1$). The sensitivity of the detector 18 to disruptions fixed on the workpiece surface and, thus, moving at the rate of travel of the moving substrate S is maximal.

Figure 2A:
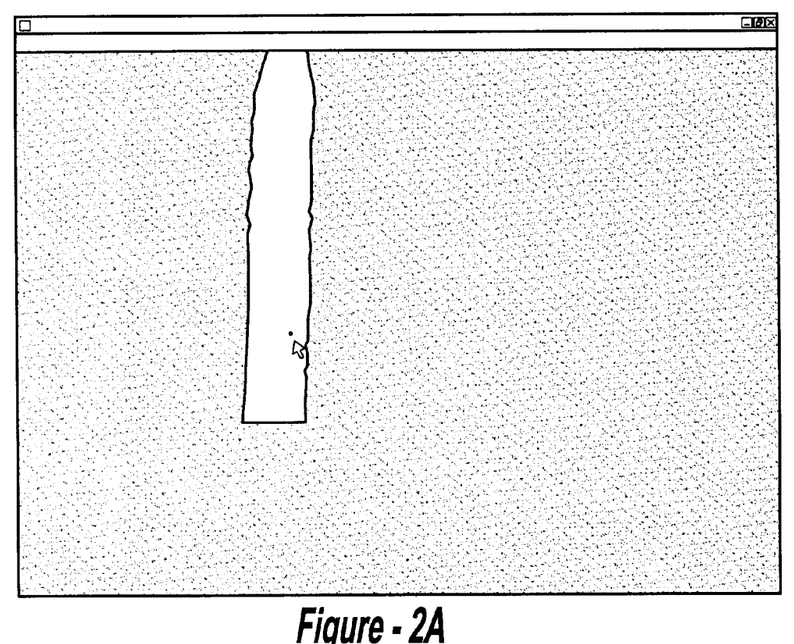
FIG. 2A is a top view of a portion of a moving substrate carrying a workpiece having a defect thereon at time $T_0$, said defect identified by the shadow it casts within a band of illumination.
Figure 2B:
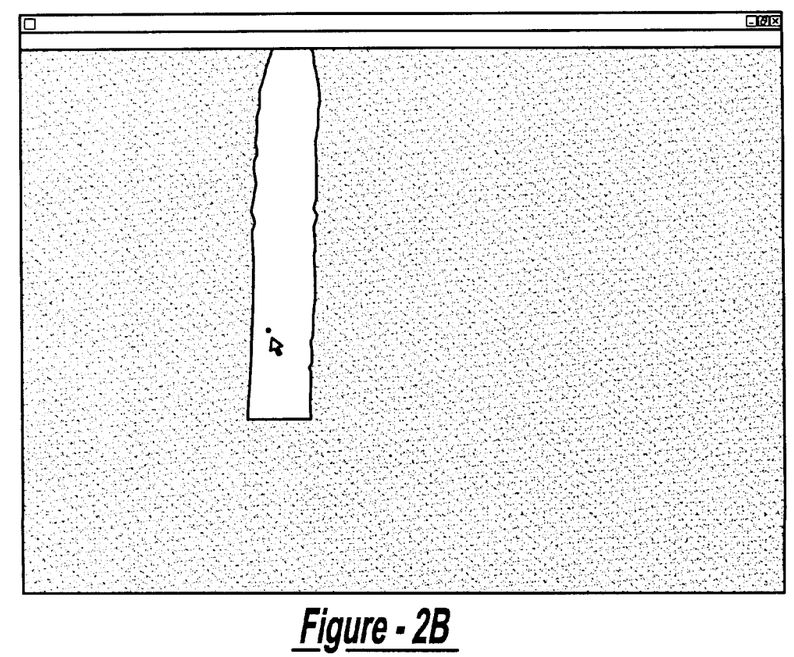
FIG. 2B is similar to FIG. 2A but shows the position of the defect at time $T_1$.
Figure 3A:
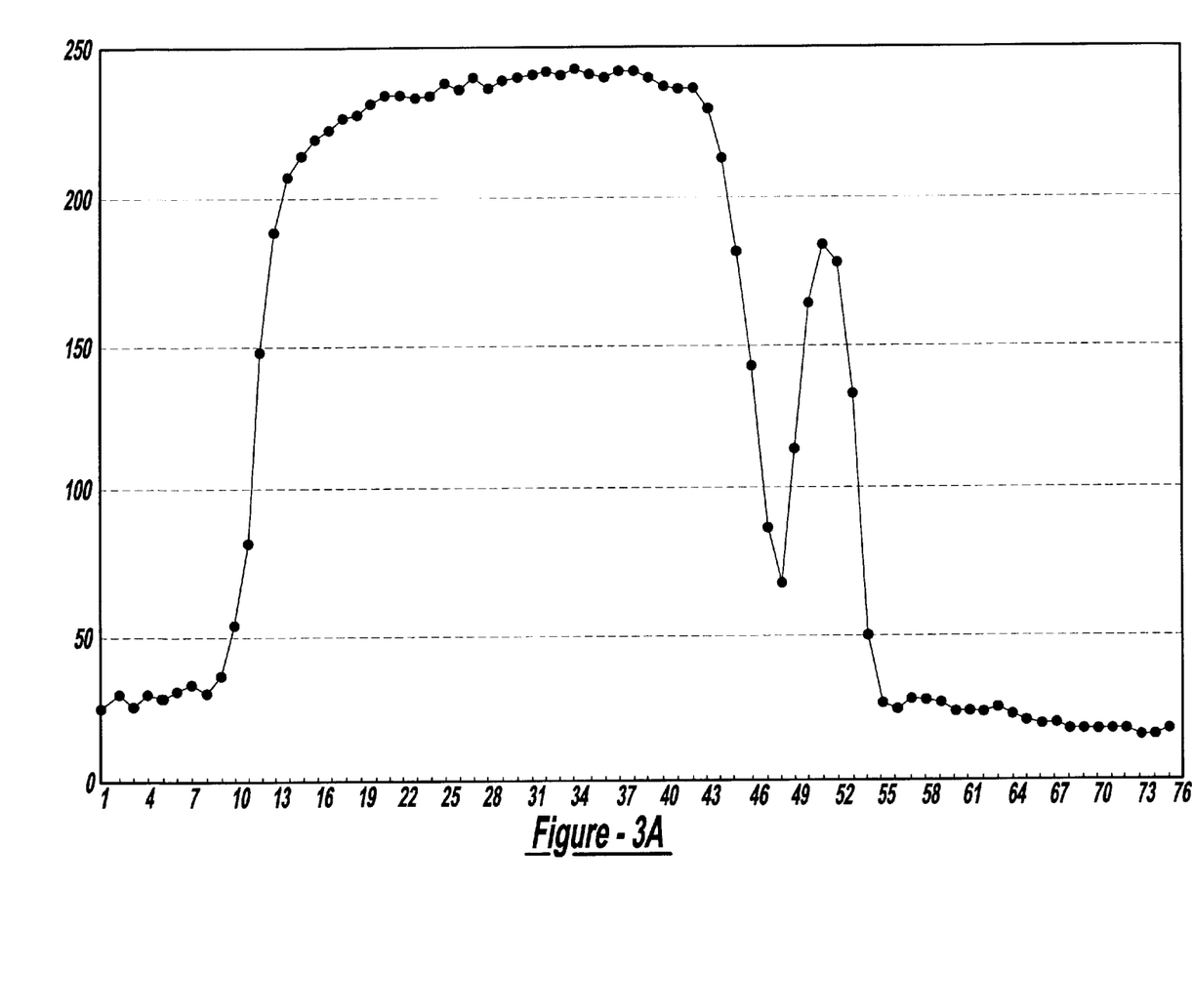
FIG. 3A is a representation of a first image of the defect of FIG. 2A at time $T_0$.
Figure 3B:
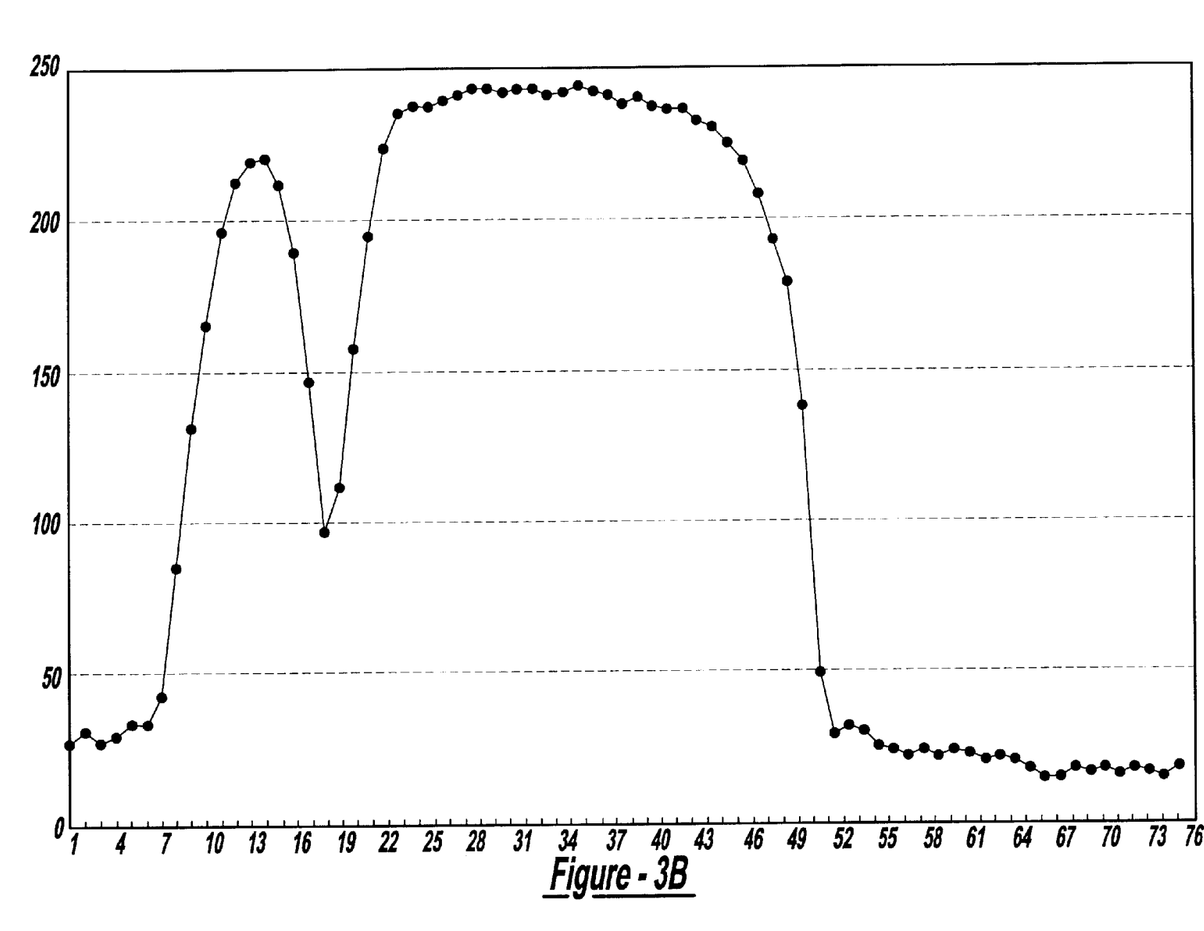
FIG. 3B is similar to FIG. 3A but represents a second image at time $T_1$.

FIGS. 3A and 3B illustrate, respectively, the correlation of the two images illustrated in, respectively, FIGS. 2A and 2B. FIG. 3A is a representation of an image showing the defect at time $T_0$, and FIG. 3B is a representation of an image showing the same defect D at time $T_1$. Defect D has moved a distance determined by the speed of the substrate S and the time $\Delta_T$ between time $T_0$ and $T_1$.

Figure 4:
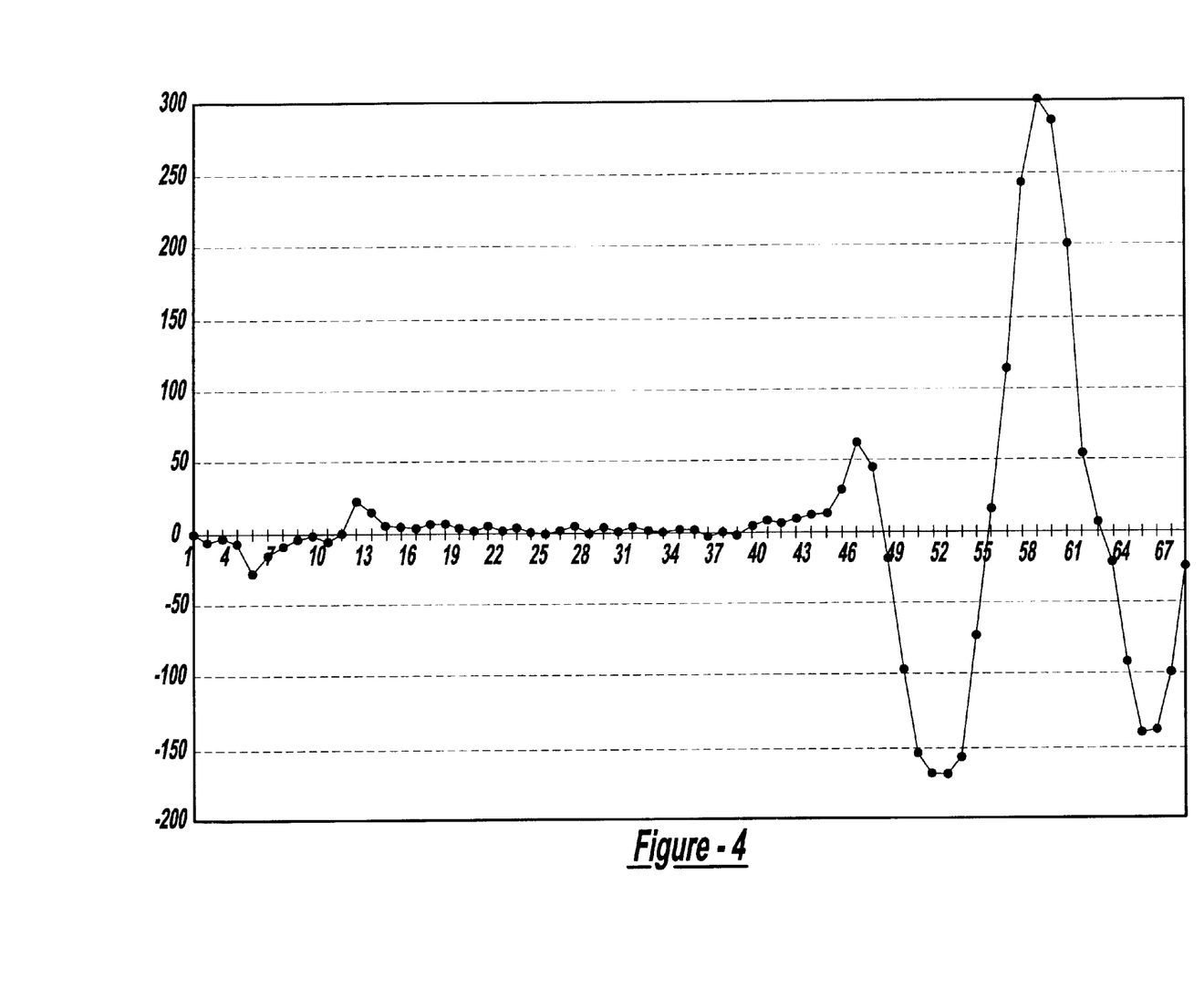
FIG. 4 shows the results of the image data of FIGS. 3A & 3B after they have been subtracted and passed through a finite impulse response filter.

The images shown in FIGS. 3A and 3B are then subject to further processing. FIG. 4 shows a composite image achieved by subtracting the image of FIG. 3B from the image of FIG. 3A and passing the result through a finite impulse response filter (FIR) designed to detect correlation. This is done electronically using the digital information stored in the computer 20 in a manner known in the prior art. The system is operative to recognize defects when a central peak such as that shown in FIG. 4 exceeds a predetermined threshold level.

Post processing of the FIG. 4 image can be performed in a number of ways depending upon the application desired. For example, the post processing software can be operative to identify the defects and classify them by size. The defects can also be classified by type; that is, whether they are craters or elevated dirt particles. Craters and bumps cast different shadow patterns which are characteristic of each type of defect. Because each defect is scanned from both sides, two sets of data representing shadow patterns for each defect are produced. These sets of shadow patterns will vary depending upon the surface elevation of the defect. For example, a bump will produce a pair of crescent shaped shadows which curve toward each other. A crater, on the other hand, will produce a reverse shadow pattern; that is, the pair of crescent shaped shadows will curve away from each other. The system of the present invention can compare the pair of shadow patterns produced by each defect with known values stored in the computer 20 and perform a closest match search for each defect detected.

Furthermore, the present system can be trained to identify known surface features of the workpieces to be inspected so that these are subtracted out and not misidentified as unexpected defects. In order to do this, the system must scan a number of workpieces having a particular surface characteristic (such as the cutout for a door handle on a side body automotive panel). The system, of course, will find a "defect" in each such workpiece at the same location and of the same type. After exposure to a sufficient number of workpieces having this same surface characteristic, the system will "learn" to expect to find that surface characteristic at that location in that particular type of workpiece. The system can then be further programmed to simply ignore the expected surface characteristic, and, instead, count as defects only irregularities which occur in unexpected locations.

Figure 5A:
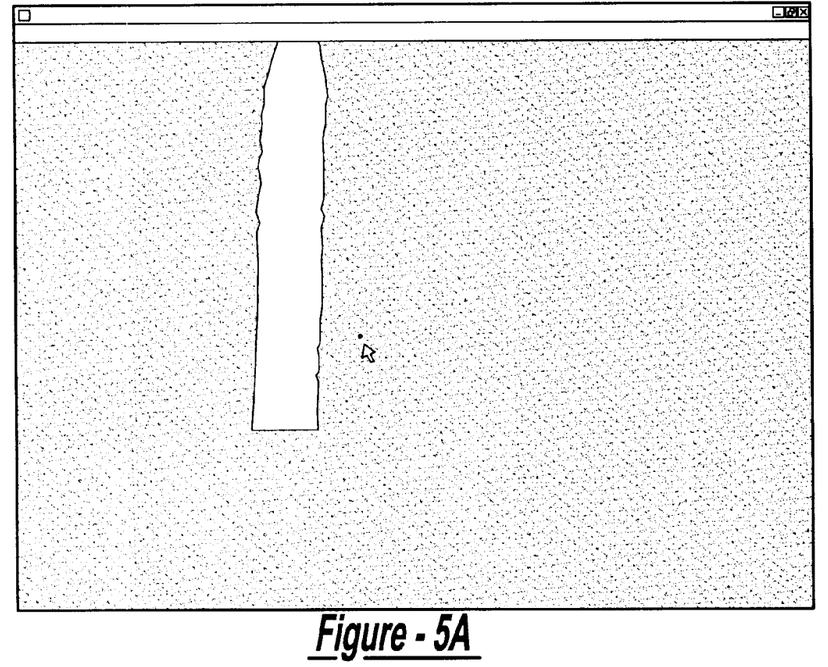
FIG. 5A is a top view of a portion of a moving substrate carrying a workpiece having a defect thereon at time $T_0$, said defect identified by the backscattered radiation it returns to the camera.

FIGS. 5A–7 illustrate how the system of the present invention can use the phenomenon of backscattering, rather than shadowing, to detect additional defects. In FIG. 5A, a defect D lies outside of the line of light. It is located in a first position at time $T_0$. FIG. 5B, which is similar to FIG. 2B, shows the defect having moved to a second position at time $T_0$ closest to the line of light. The system 10 captures successive images of the defect D at times $T_0$ and $T_1$.

Figure 5B:
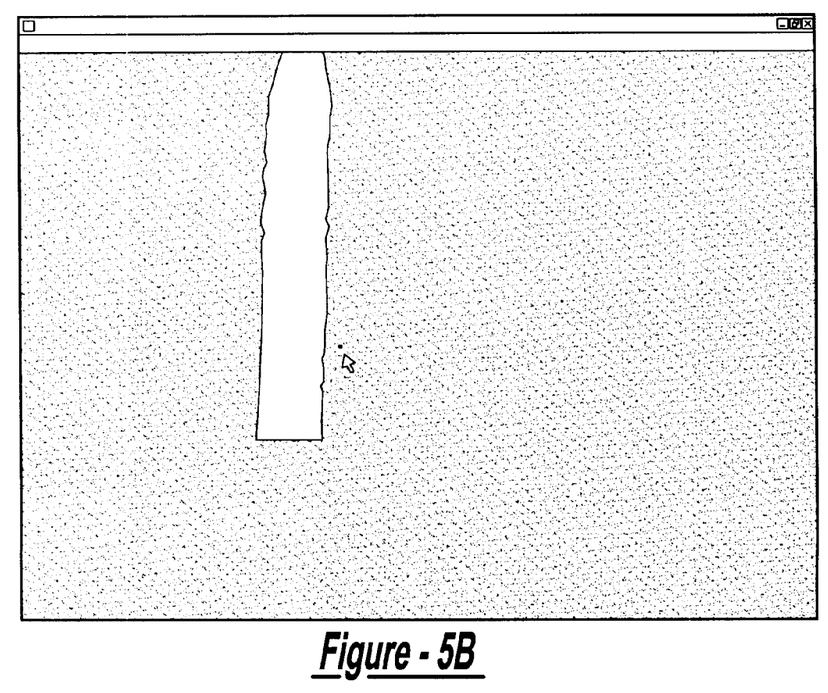
FIG. 5B is similar to FIG. 5A but shows the position of the defect at time $T_1$.
Figure 6A:
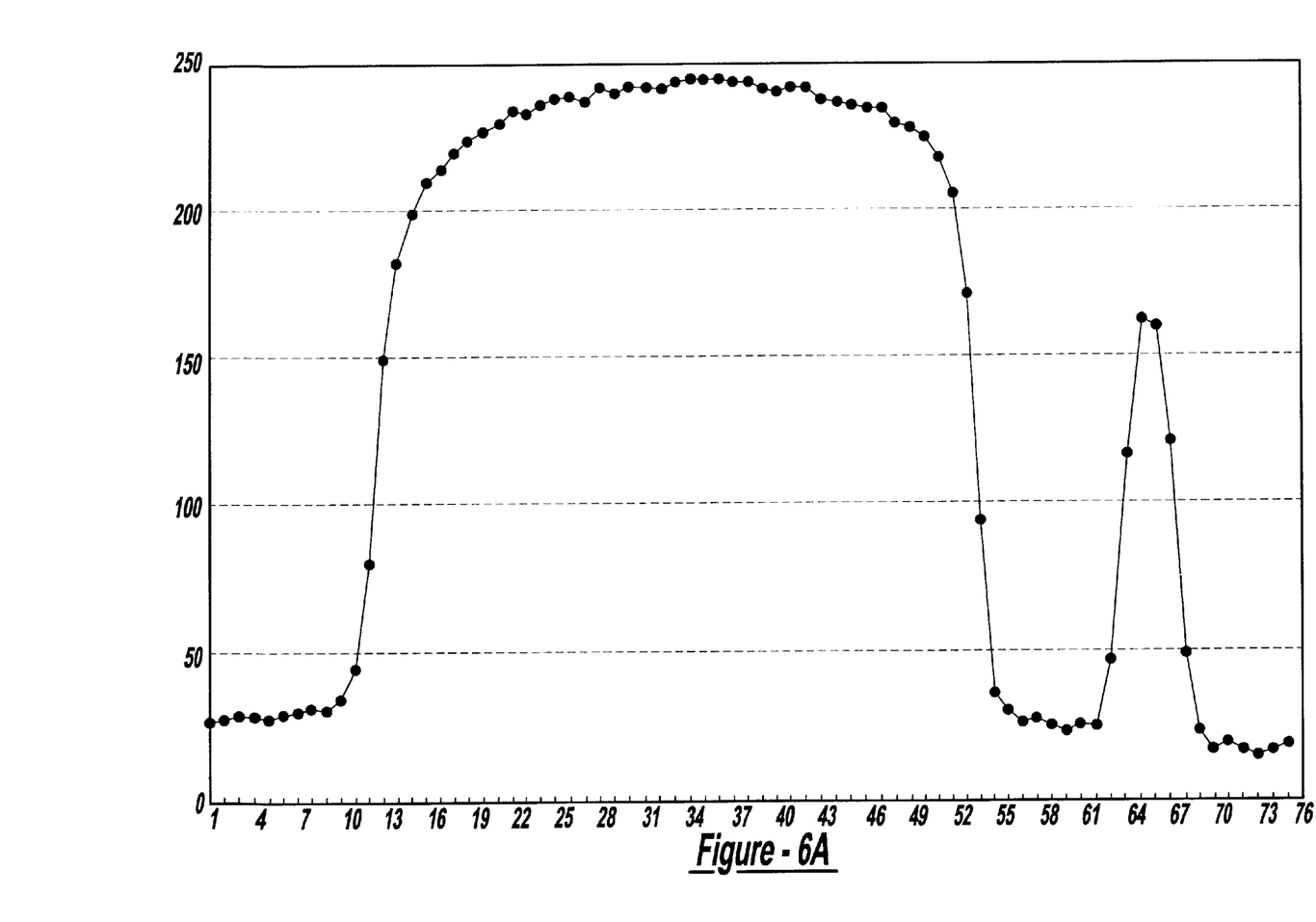
FIG. 6A is a representation of a first image of the defect of FIG. 5A at time $T_0$.
Figure 6B:
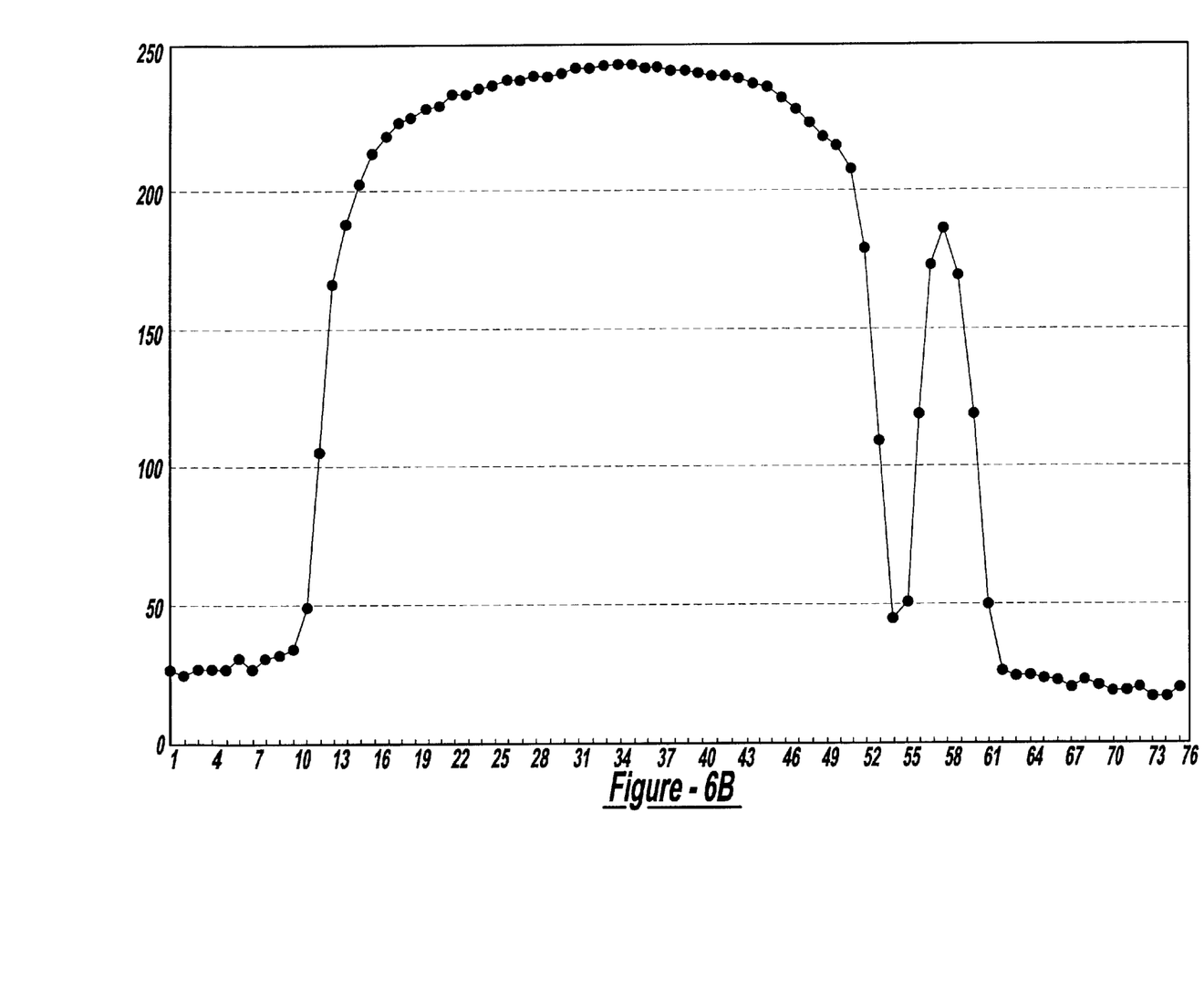
FIG. 6B is similar to FIG. 6A but represents a second image at time $T_1$.

FIGS. 6A and 6B illustrate, respectively, the correlation of the two images illustrated, respectively, in FIGS. 5A and 5B. FIG. 6A is a representation of an image showing the backscattering defect at time $T_0$, and FIG. 6B is a representation of an image showing the same defect at time $T_1$.

Figure 7:
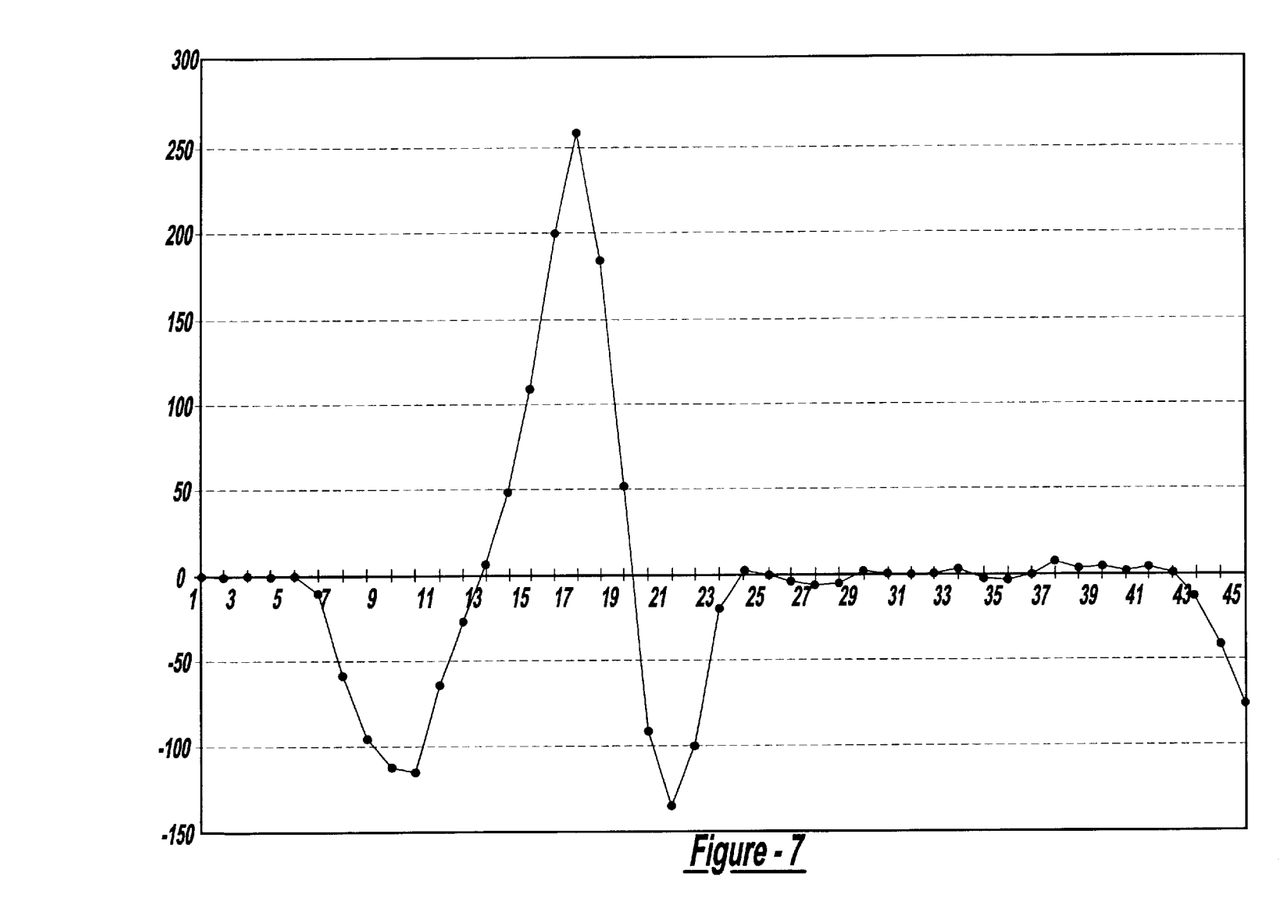
FIG. 7 shows the result of the image data of FIGS. 6A and 6B after they have been subtracted and passed through a finite impulse response filter.

In a manner analogous to the processing done in the case of the shadowed defect of FIG. 2A and FIG. 2B, FIG. 7 shows a composite image achieved by subtracting the image of FIG. 6B from the image of FIG. 6A and passing the result through a FIR. It should be noted that it is very easy for the system of the present invention to operate to detect both backscatter and shadow defects. This is so because the electronic processing which is performed for the two types of defects can be carried on by using the same algorithms. The only difference between the two types of defect detection is that in one case, the values are all positive, and in the other case they are all negative. Thus, in a particularly preferred embodiment, the system 10 is programmed to perform both types of detection.

The use of backscattered light in defect detection has certain advantages over the detection of shadows cast by defects. The detection of shadowing requires even illumination. This is difficult to achieve because the illumination must be wide, even and bright. It is particularly hard to achieve such even illumination on a contoured surface.

The detection of defects by shadowing also requires that the detector receive light which is sharply angled with respect to the plane of the surface. Otherwise, the resolution of the image is compromised. On flat, even surfaces, maintaining a low angle of incidence and reflection is relatively easy. However, many workpieces, and particularly automotive body panels, are highly contoured. The use of shadowing, alone, does not produce completely satisfactory results under these conditions.

In contrast, backscatter merely requires a small source of illumination. The source does not have to be even or large, but can be any bright source of diffuse light, such as a simple fluorescent fixture. Moreover, the resolution of the image does not depend upon a sharp angle. In fact, the light source can be perpendicular to the surface. Thus, we have found that the detection of defects by employing the present system to detect backscattering detects considerably more defects than the use of shadowing alone.

There are, in certain cases, some defects that are picked up more easily by detecting their shadows. This is particularly true of flat surfaces. Hence, an optimal result may occur if, as previously described, both types of defects are detected. The most expedient way to do this is simply to split the data stream into two identical portions. The algorithm for detecting backscatter is applied to one data stream, and the algorithm for detecting shadowing is applied to the other data stream. This requires only slightly more computational time than simply doing either kind of analysis, alone.

Figure 8:
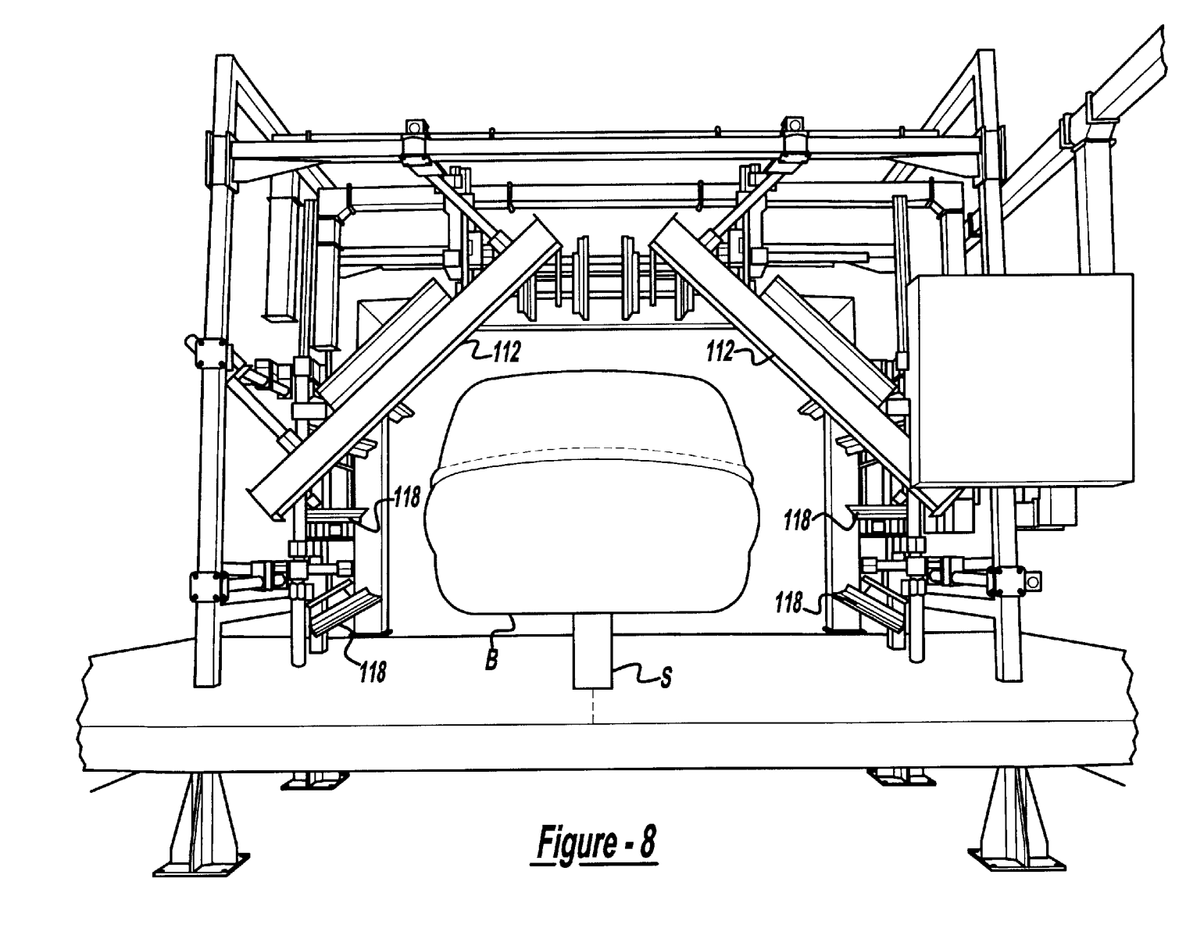
FIG. 8 is a front view of a vehicle inspection installation employing the system of the present invention.

FIG. 8 is a front view of a vehicle inspection installation, in which a plurality of light sources 112, each with its associated detectors in the form of video cameras 118, are used. The light sources and video cameras are arranged so as to image all portions of an automotive body B which is conveyed through the system by means of conveyor belt substrate S. In the embodiment depicted in FIG. 8, the light sources 112 are tented in angular relationship with respect to the auto body B so as to form a sort of "roof" over the succession of workpieces. Alternatively, the light sources 112 could be arranged to form a closed arch over the workpieces. The particular arrangement is not critical so long as the plurality of light sources are placed so that they illuminate each portion of the automotive body passing through the system.

Similarly, the cameras 118 depicted in the FIG. 8 embodiment are disposed along each side of the car passing through the system. The cameras 118 are arranged and located so that the light reflected or scattered from the light sources from all portions of the vehicle body will be imaged. The optimum arrangement of the light sources and cameras in any particular installation is considered to be within the ambit of one of skill in the art. Thus, the system illustrated in FIG. 8 is simply one possible arrangement out of many, that could be designed.

What has been described is a system and method for performing automated inspection to detect dirt and other flaws on the painted surfaces of a succession of workpieces. The system uses a line of light which falls onto a moving substrate carrying the workpieces. A detector is operative to view across the moving substrate such that two separate images are captured of each location on the workpiece. The shadows cast by the defects or light backscattered from them cause variations in the amplitude of light scattered by the workpiece surface which are detected by the detector. The signals from the scanning detector are then digitized and subjected to further processing to identify the defects, and characterize them by size and type.

While the present invention has been described with reference to certain exemplifications and embodiments thereof, it is to be understood that the present invention may be otherwise implemented. Thus, one of skill in the art in designing automated systems may vary the depicted and described embodiments without departing from the scope of the present invention. It is the claims appended hereto, and all reasonable equivalents thereof, rather than the exact depicted embodiments and exemplifications, which define the true scope of the present invention.

We claim:

1. A system for detecting defects on a coated surface, the system comprising:
   a source of diffuse light arranged for emitting an elongated line of light having a leading edge and a trailing edge onto a moving substrate having a direction of travel substantially perpendicular to said line of light such that said substrate passes therethrough, a workpiece to be inspected being supported by said moving substrate;
   an area detector for viewing said substrate and capturing images of the received light scattered by a surface of said workpiece, said detector being operative to view a portion of the surface of the workpiece including that illuminated by said line of light, said detector having a frequency of operation selected so that each portion of the surface of said workpiece is imaged at least twice during said workpiece's traversal through the field of view of the detector;
   means for generating digital signals, including first and second sets of digital signals corresponding to the amplitude of scattered light received by said detector during said two captured images of a portion of said workpiece; and
   means for comparing said first and second sets of digital signals to isolate and amplify variations in the amplitude of received light caused by a defect in said workpiece surface, wherein the means for comparing said first and second sets of digital signals includes substracting first and second sets of digital signals one from the other to form a composite set of digital signals and applying a finite impulse response filter to the composite set of digital signals such that the filter is designed to detect correlation in accordance with the speed of the workpiece and the time between the two captures images.

2. The system of claim 1 wherein said defect characteristic size.

3. The ststem of claim 1 wherein said defect characteristic surface elevation.

4. The system of claim 1 wherein said detector is a charge coupled device detector.

5. The system of claim 1 further comprising means for comparing said isolated and amplified signal with stored values representing known workpiece surface irregularities so that the system is able to distinguish between known surface irregularities and a surface defect.

6. The system of claim 1 wherein said detector is a CCD camera, said two captured images of a portion of said workpiece occurring during the traversal of said portion of the workpiece through said line of light.

7. The system of claim 6 further comprising means for comparing said isolated and amplified signal with stored values representing known workpiece surface irregularities so that said system is able to distinguish between known surface irregularities and a surface defect.

8. The system of claim 1 wherein said detector is a OCD camera, said two captured images of a portion of said work piece occurring during the traversal of said portion of the workpiece outside of the line of light.

9. The system of claim 8 further comprising means for comparing said isolated and amplified signal with stored values representing known workpiece surface irregularities so that said system is able to distinguish between known surface irregularities and a surface defect.

10. The system of claim 1 further including means for processing said isolated and amplified signal to identify at least one characteristic of said surface.

11. A method for detecting defects on a painted surface, the method comprising the steps of:
    emitting an elongated line of light having a leading edge and a trailing edge;
    passing a moving substrate through said line of light in a direction of travel substantially perpendicular thereto, said substrate supporting at least one workpiece to be inspected;
    imaging with a detector an area of said substrate that includes said line of light to receive light scattered by a surface of said workpiece;
    operating the system at a frequency of operation selected so as to image each portion of said workpiece at least twice during said workpiece's traversal through the field of view of the detector;
    generating digital signals, including first and second sets of digital signals corresponding to the amplitude of scattered light received by said detector during, respectively, said first and second images;
    substracting first and second sets of digital signals one from the other to form a composite set of digital signals; and
    applying a finite impluse response filter to the composite set of digital signals such that the filter is designed to detect correlation in accordance with the speed of the workpiece and the time between the two captures image, thereby isolating variations in the amplitude of received light caused by a defect in said workpiece surface to identify a surface detect.

12. The method of claim 11 wherein the step of identifying defect further comprises the step of identifying the size of said defect.

13. The method of claim 11 wherein the step of identifying a surface defect further comprises the step of identifying the surface elevation of said defect.

14. The system of claim 11 wherein the step of imaging said substrate further comprises the step of imaging said substrate with a charge coupled device detector.

15. The system of claim 11 further comprising the step of comparing said isolated and amplified signal with stored values representing expected workpiece surface irregularities to distinguish between expected surface irregularities and a surface defect.

* * * * *

UNITED STATES PATENT AND TRADEMARK OFFICE
CERTIFICATE OF CORRECTION

PATENT NO.     : 6,462,813 B1
DATED          : October 8, 2002
INVENTOR(S)    : G. Neil Haven et al.

It is certified that error appears in the above-identified patent and that said Letters Patent is hereby corrected as shown below:

Column 10,
Line 1, "claim 1" should be -- claim 10 --.
Lines 1-2, after "characteristic" insert -- is --.
Line 3, "ststem" should be -- system --.
Line 3, "claim 1" should be -- claim 10 --.
Line 3, after "characteristic" insert -- is --.
Line 20, "OCD" should be -- CCD --.
Line 31, after "surface" insert -- defect --.
Lines 62-63, after "identifying" insert -- a surface --.

Signed and Sealed this

Twenty-third Day of December, 2003

JAMES E. ROGAN
*Director of the United States Patent and Trademark Office*